United States Patent [19]
America et al.

[11] Patent Number: 5,270,125
[45] Date of Patent: Dec. 14, 1993

[54] BORON NUTRIDE MEMBRANE IN WAFER STRUCTURE

[75] Inventors: William G. America, Newtown; Richard R. Poole, Norwalk, both of Conn.

[73] Assignee: Redwood Microsystems, Inc., Menlo Park, Calif.

[21] Appl. No.: 782,705

[22] Filed: Oct. 25, 1991

Related U.S. Application Data

[60] Division of Ser. No. 540,043, Jun. 21, 1990, Pat. No. 5,066,533, which is a continuation-in-part of Ser. No. 377,979, Jul. 11, 1989, abandoned.

[51] Int. Cl.$^5$ .......................... B32B 9/00; G03F 9/00
[52] U.S. Cl. .................................. 428/698; 428/172; 428/192; 428/699; 428/704; 430/5; 378/34; 378/35
[58] Field of Search .................. 430/5; 428/698, 699, 428/192, 704, 131, 156, 172, 33; 378/34, 35

[56] References Cited
U.S. PATENT DOCUMENTS 4,868,093  9/1989  Levy ............................ 430/966

Primary Examiner—Donald J. Loney
Attorney, Agent, or Firm—Flehr, Hohbach, Test, Albritton & Herbert

[57] ABSTRACT

A laminated structure includes a wafer member with a membrane attached thereto, the membrane being formed of substantially hydrogen-free boron nitride having a nominal composition $B_3N$. The structure may be a component in a mechanical device for effecting a mechanical function, or the membrane may form a masking layer on the wafer. The structure includes a body formed of at least two wafer members laminated together with a cavity formed therebetween, with the boron nitride membrane extending into the cavity so as to provide the structural component such as a support for a heating element or a membrane in a gas valve. In another aspect borom is selectively diffused from the boron nitride into a <100> surface of a silicon wafer. The surface is then exposed to EDP etchant to which the diffusion layer is resistant, thereby forming a channel the wafer member with smooth walls for fluid flow.

10 Claims, 2 Drawing Sheets

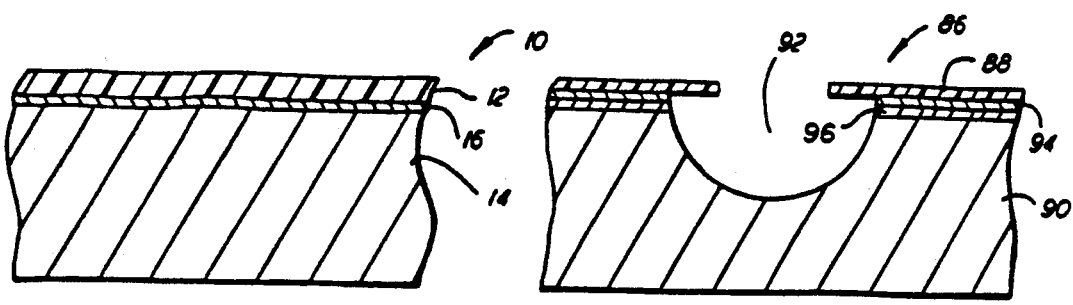
FIG. 1
FIG. 4
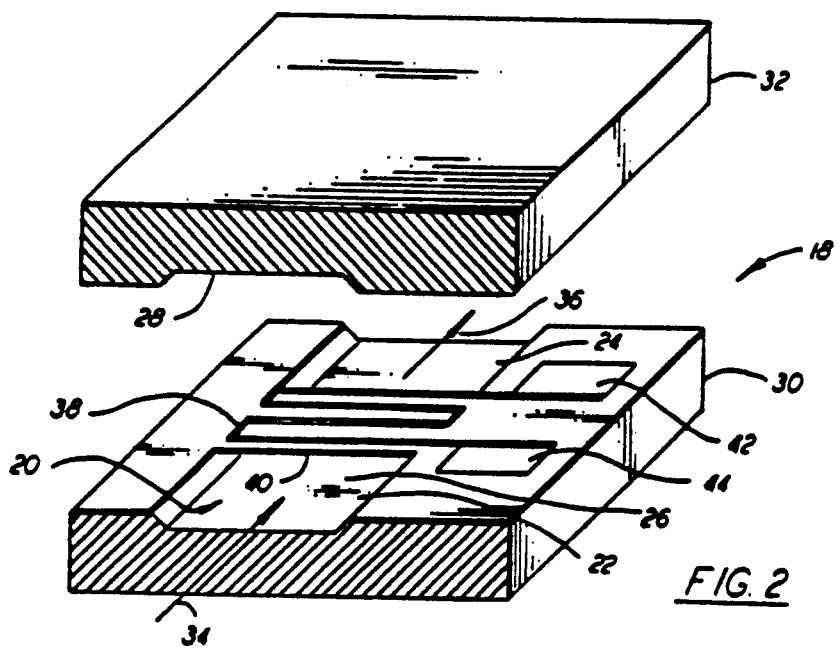
FIG. 2
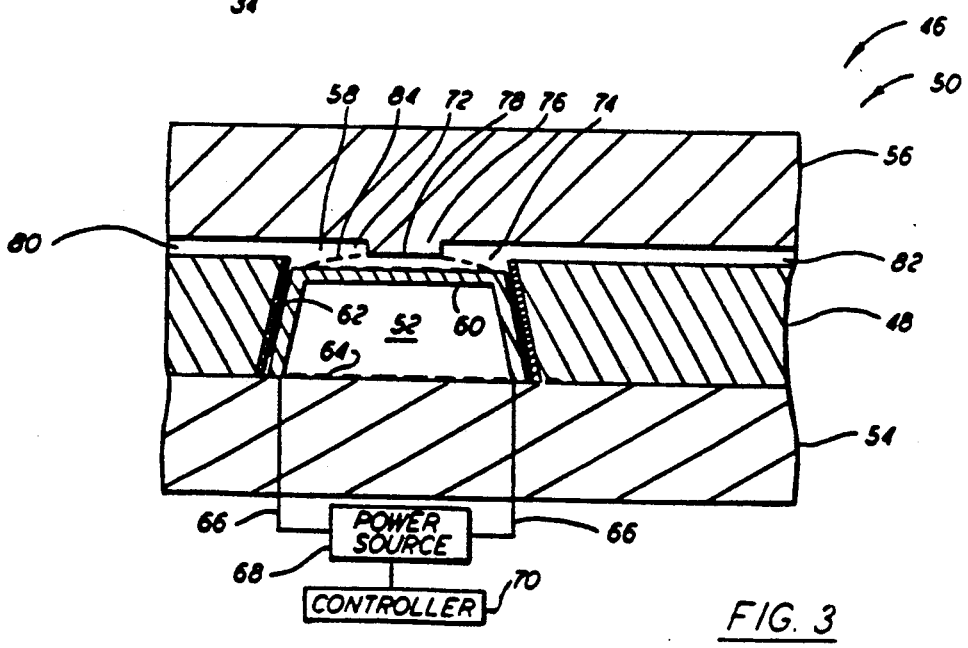
FIG. 3

BORON NUTRIDE MEMBRANE IN WAFER STRUCTURE

This is a division of application Ser. No. 07/540,043, filed Jun. 21, 1990, now U.S. Pat. No. 5,066,533, which is a continuation-in-part of application Ser. No. 07/377,979, filed Jul. 11, 1989.

This invention relates to miniature devices and particularly to laminated structures including a membrane.

BACKGROUND OF THE INVENTION

Miniaturized devices have been suggested for effecting various mechanical functions. Such devices are fabricated utilizing the techniques of integrated electronic circuit production, as described, for example, in an article "Silicon as a Mechanical Material" by K. E. Petersen, Proc. IEEE 70, 420–457 (May 1982). One field of application of the device components is gas chromatography, in which chromatographic columns, injectors, valves and detectors are integrated into a device formed primarily of laminated silicon wafers. The reference discloses a hot wire detector in which the thin film heater is supported by a silicon membrane in a chamber duct of flowing gas. It is necessary that membranes utilized in such devices have good rigidity, at least some flexibility and, in some critical areas, high temperature stability.

The reference also describes a solenoid valve. An improved valve for such a system is disclosed in "A Microminiature Electric-to Fluidic Valve" by M. J. Zdeblick and J. B. Angell, *Transducers* 87, pp 827–829 (1987). The valve utilizes a sealed cavity filled with a liquid. One wall of the cavity is formed with a flexible membrane which can press against a pneumatic nozzle. When the liquid is heated, its pressure increases, pushing the membrane toward the nozzle and turning off the valve.

Silicon nitride is mentioned in the Peterson reference as a masking material, and is suggested for use in strain sensors as disclosed in "Deposition Techniques and Properties of Strain Compensated LPCVD Silicon Nitride Films" by H. Guckel, D. K. Showers, D. W. Burns and C. R. Rutigliano, *Technical Digest*, IEEE Solid State Sensors (Jun. 2–5, 1986). A problem with silicon nitride is that its coefficient of thermal expansion is about half that of silicon, with a corresponding tendency to stress rupture.

Boron nitride deposited by chemical vapor deposition (CVD) is used as a component material as a mask for etching silicon as taught in "Boron Nitride Mask Structure for X-Ray Lithography" by D. Maydan, G. A. Coquin, H. J. Levinstein, A. K. Sinha and D. N. K. Wang, *J. Vac. Sci. Technol* 16 (6) 1959 (1979). CVD boron nitride is generally in the form of BN and, due to the chemical process, contains hydrogen. The hydrogenated BN changes stress with time and temperature, becoming very tensive to the point of rupture.

Greater precision is always a goal in producing such devices, particularly for further miniaturization. In the case of fluid flow devices, smoothly rounded channels are important to minimize resistance to flow and allow more precise control over cross sectional areas. However, conventional masking for etchants tends to produce an undesirable form of anisotropic etching, resulting in nonuniformity of etched channels. For example etching of a <100> silicon wafer having a mask of silicon dioxide or boron nitride, results in outside corners being etched with additionally tilted faces from <110> and <310> planes, and inside corners being perpendicular sharp corners. Although smooth channels are depicted in the literature, in practice actually etched channels and cavities are not so smooth. In chromatographic operation sharp inside corners may result in peak distortion caused by flow trapping in a corner.

Therefore, objects of the present invention are to provide an improved laminated structure for use in miniaturized devices, to provide a laminated structure with an improved masking layer, to provide a novel membrane material for laminated structures, to provide improved miniature mechanical devices including a gas flow detector and a gas valve, and to provide a process for forming a novel membrane material on a wafer.

Further objects of the present invention are to provide a novel process for forming a mask on a silicon wafer and to provide an improved mask thereby, to provide an improved boron diffusion layer on silicon useful for masking against certain etchants, and to provide a process that allows favorable anisotropic etching for forming smoothly rounded channels in the silicon surface.

SUMMARY OF THE INVENTION

The foregoing and other objects are achieved by a laminated structure comprising a wafer member with a membrane attached thereto, the membrane being formed of substantially hydrogen-free boron nitride having a nominal composition $B_3N$. The structure is advantageously a component in a mechanical device for effecting a mechanical function. According to one aspect of the invention the structure comprises a body formed of at least two wafer members laminated together with a cavity formed therebetween, with the boron nitride membrane extending into the cavity so as to provide the structural component. Preferably the wafer member is formed of single crystal silicon, and a silicon dioxide film may be disposed as a bonding layer between the boron nitride membrane and the wafer member. Alternatively the boron nitride membrane is in the form of a masking layer on the wafer member for masking etching of the wafer member.

The objects are further achieved by a process for forming a boron nitride membrane on a wafer member, comprising depositing by low pressure chemical vapor deposition a hydrogenated boron nitride film on a wafer member, and heating the boron nitride film in an environment free of hydrogen and oxygen at a sufficiently high temperature and for a sufficient time period to transform the boron nitride film to substantially hydrogen-free boron nitride having a nominal composition $B_3N$.

In another aspect of the invention, foregoing and other objects are also achieved by a process for forming a step with a smooth wall in a wafer member, comprising diffusing boron into a portion of a selected area of a <100> surface of a silicon wafer member to form a boron diffusion layer, and exposing the selected area to a selective etchant to which the boron diffusion layer is resistant. The unetched boron diffusion layer thereby forms a step adjacent etched silicon in the wafer member with a smooth wall substantially perpendicular to the <100> surface. The smooth wall may define a side of a fluid flow channel with smoothly rounded contours.

BRIEF DESCRIPTION OF THE DRAWINGS

FIG. 1 is a cross section of a laminated structure of the invention.

FIG. 2 is exploded perspective of a gas thermal conductivity detector utilizing the invention.

FIG. 3 is a cross-section of a gas valve utilizing the invention.

FIG. 4 is a cross section of a laminated structure including a masking layer according to the invention.

DETAILED DESCRIPTION OF THE INVENTION

Figure 6:
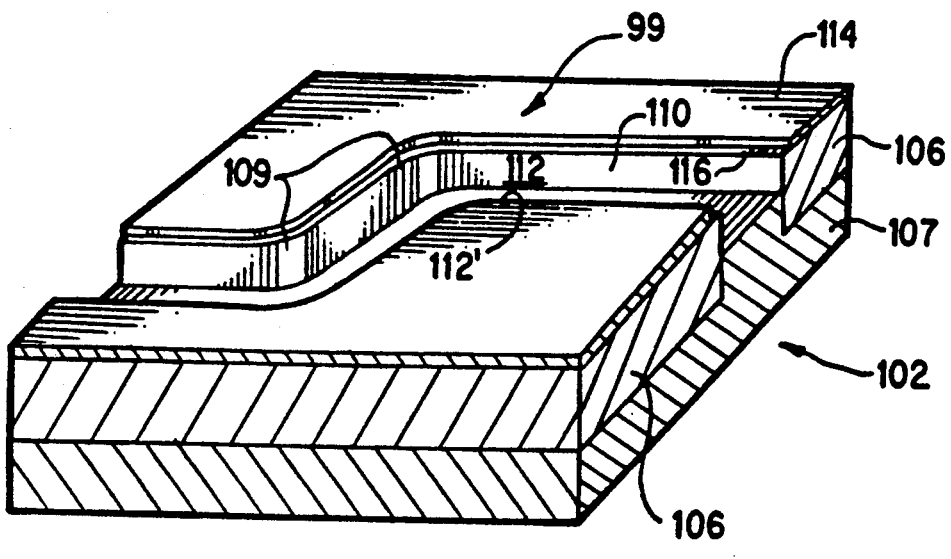
FIG. 6 is a perspective of a portion of a miniaturized device formed according to the invention.

FIG. 1 depicts a portion of a miniaturized laminated structure 10 in a simple mode, in which a membrane 12 is formed on a wafer member 14. The membrane is advantageously formed on a wafer member of single crystal silicon. An intermediate layer 16 may also be formed between the membrane and the wafer. The intermediate layer may be silicon dioxide or, as explained below, a modified form of the membrane material.

According to the present invention the membrane is formed of boron-rich, substantially hydrogen-free boron nitride having a nominal composition $B_3N$. Preferably this is produced by a process comprising depositing by low pressure chemical vapor deposition a hydrogenated boron nitride film on a wafer, the film being nominally $BNH_3$. The film is heated in an environment free of hydrogen and oxygen at a sufficiently high temperature and for a sufficient time to transform the boron nitride film to substantially hydrogen-free boron nitride having a composition nominally $B_3N$, generally between about BN and $B_3N$. A suitable temperature is between about 1050° C. and 1150° C., and the time should exceed about one hour, e.g. up to about 12 hours. Preferable conditions are 1100° C. in nitrogen or vacuum for 4 hours. The resulting membrane may be between 1 and 15 microns thick, depending on application.

The initial hydrogenated boron nitride film is deposited by conventional low pressure chemical vapor deposition (LPCVD) of BN type boron nitride. This is effected on a precleaned (as by conventional etching) silicon wafer by reacting a gas containing 5 mols of ammonia and 1 mol of diborane at 340° C. for 10 to 25 hours depending on desired thickness, using nitrogen as a carrier gas.

It is particularly useful for the boron nitride membrane to be applied to silicon because such a substrate is conveniently etched to fabricate mechanical devices. Also the boron-rich nitride of the invention matches silicon very well in thermal expansion, favorable for maintaining bonding in varying temperature conditions.

Formation of the transformed boron nitride membrane directly on silicon generally results in a well defined intermediate layer 16 of boron doped silicon, the boron concentration being about $10^{21}$ to $10^{22}$ atoms/cm$^3$. This intermediate layer is about 1.0 to 50 microns thick and provides excellent bonding for the membrane.

If the depleted boron nitride intermediate layer is not desired, a silicon dioxide film may be disposed to form layer 16 between boron nitride membrane 12 and silicon wafer member 14. A thickness of the film of about one micron is sufficient to act as a diffusion barrier for boron. The oxide layer is formed prior to the initial deposition of boron nitride. Oxide formation is by conventional means such as, after cleaning the silicon surface, heating the wafer in air or oxygen to 1100° C. for 2 hours. The initial boron nitride layer then is deposited as described above. The boron nitride bonds to the oxide very well.

According to one aspect of the invention a laminated structure of the wafer and boron-rich, hydrogen-free boron nitride is utilized as a component in a mechanical device for effecting a mechanical function. In such a case the structure may comprise a body formed of at least two wafer members laminated together with a cavity formed therebetween, with the boron nitride membrane extending into the cavity so as to provide a structural component. One wafer member is preferably silicon and the other may also be silicon or may be quartz or a high silica glass such as Pyrex TM. The component may be stationary or may have a moving part, and in particular the membrane may be utilized in a flexing or other motion.

As an example of a stationary component incorporating the invention, in one preferred embodiment the mechanical device is a detector for measuring thermal conductivity of a gas. FIG. 2 illustrates a hot wire type of gas thermal conductivity detector 18 of the general type disclosed in the Petersen article. A detector cavity 20 has a gas inlet 22 and an outlet 24. The cavity is conveniently formed by adjacent grooves 26,28 etched in adjacent wafers 30,32. A flowing gas is shown by arrows 34,36. A hot wire electrical resistive element 38 formed conventionally as a thin film of platinum or the like is deposited in a serpentine path on a bridge 40 formed of hydrogen free, $B_3N$ boron nitride, e.g. 2–3 microns thick. The bridge divides grooves 26 and 28. Electrical connections 42,44 for current and voltage measurement are provided for the element. Change in thermal conductively of the flowing gas, is detected by the corresponding change of resistance of the thin film resistance and is measured by voltage measurement such as with a Wheatstone bridge.

In another embodiment illustrating a movable membrane the mechanical device incorporating the membrane is a fluid valve. One such valve 46 shown in FIG. 3. A middle wafer 48 of a laminate 50 has therein a first cavity 52 closed off by a bottom wafer 54. An upper wafer 56 has therein a second cavity 58 adjacent to cavity 52. A membrane 60 of hydrogen-free $B_3N$ is disposed in laminate body 50 so as to separate the first and second cavities. Other layers 62 of depleted boron nitride or silicon dioxide may be used for bonding the boron nitride to wafer 48. Electrical heating element strips 64 of aluminum or the like for operating the valve are also deposited adjacent cavity 52 on bottom wafer 54 and connected by electrical leads 66 to a source 68 of electrical current responsive to a controller 70 which may be incorporated as integrated electronic circuits into the overall device. Upper cavity 58 is divided into an inlet portion 72 and an outlet portion 74 by a protrusion 76 extending from upper wafer 56 to a surface location 78 proximate membrane 60 but spaced slightly therefrom. An inlet gas passage 80 etched into wafer 56 extends to the inlet cavity and an outlet gas passage 82 extends from the outlet cavity. The valve will also be useful for liquid.

Lower cavity 52 is filled with a medium such as liquid methyl chloride as disclosed in Zdbelick et al, which will expand significantly when heated by element 64, preferably by partially vaporizing. The expansion will cause membrane 60 to distend into the upper cavity, as shown by broken lines 84, to a sealing surface at location 78 on protrusion 76 to close off outlet portion 74 from inlet portion 72. Thus in a non-distended, relaxed position the membrane allows gas to flow between the passages, and current to the heating element results in the membrane distending to close off gas flow.

According to a further aspect of a laminated structure 86 of the invention the boron nitride membrane is formed as a mask 88 on a wafer member 90 for masking etching of a groove 92 of the wafer member, FIG. 4. The membrane for this purpose may be relatively thin, e.g. 1 microns. A silica layer 94 may be present and an intermediate, boron diffusion layer 96 also may be present but minimal (0.5 microns) due to the silica barrier. The membrane is deposited, converted and then conventionally masked such as with a photoresist. The membrane then is selectively patterned with an etchant that does not attack the silicon wafer, for example with $CF_4/O_2$ (96:4 volume) as a reactive ion source, exposed at 100 mtorr, 30 cc/min flow, 100 watts RF. The boron nitride is immune to ordinary etchant environments for the silicon. Such etchants include EDP (ethylene diamine-pyrocatechol), KOH (40 vol % at 90° C.) and HNA (hydrofluoric, nitric and acetic acids—8:2:1).

Selective etching to produce a pattern in the membrane may be effected in other ways. One is to remove the initial $BNH_3$ film from a selected portion of the wafer surface prior to heating the wafer with the film to the high temperature for the appropriate time period. The step of removing the film comprises the substeps of selectively applying a premask layer of a conventional photoresist onto the intended remaining portion of the boron nitride film.

A cyclic deflection test was run on a boron membrane formed according to the invention, 2.5 cm diameter and 2 microns thick. It was vibrated acoustically at its resonant frequency of 1.8 MHz. The vibrational deflection of +/−3 microns remained unchanged for the duration of the test which was 6 billion deflections, indicating no significant work hardening. It is estimated that this cycling was the equivalent to 10 years of normal operation in a valve at 8 hours per day, 5 days per week.

The transformed boron nitride is thermally stable for long periods of time at elevated temperatures exceeding 400° C. and retains a low stress of about $2 \times 10^9$ dynes/cm. This characteristic and membrane rigidity are particularly suitable for a membrane to support or be proximate to electrically heated films for such applications as described above. Platinum film filaments deposited on the membrane about 0.5 microns thick are a further example.

As mentioned above, formation of the transformed boron nitride membrane directly on clean silicon results in a well defined intermediate layer 16 (FIG. 1) which consists essentially of boron diffused in silicon, i.e. boron doped silicon. In the case of no silica barrier layer, under the preferred heat treatment it was found that diffusion of the boron into <100> oriented silicon occurs at a linear rate of about one micron per minute for at least 25 minutes, i.e. to 25 microns thickness. Further thickness of diffusion is expected to occur up to at least 50 microns. According to a further embodiment this diffusion layer may be used advantageously as a secondary masking layer, or as a primary mask with the $B_3N$ layer fully or selectively removed, or as a standing component of the silicon device as explained below.

To operate as a good mask, resistant to etchant, the boron should be present in the silicon in a concentration of at least about $10^{19}$ atoms/cm$^3$, but should not fully replace the silicon, the maximum boron being about $1 \times 10^{23}$, referenced to a neat silicon density of about $6 \times 10^{23}$. A concentration achieved according the preferred conditions described above, and indeed a preferred concentration, is about $10^{22}$ atoms/cm$^3$.

The masking layer of diffused boron is especially useful for the etchant ethylene diame-pyrocatechol (EDP) in water in proportions E 35.1 mole %, D-P 3.7 mole % and $H_2O$ 61.2 mole %, with the addition of pyrazine 2 g/l of solution. This is preferably used at about 118° C. for 5 to 120 minutes. Silicon etchant is about 2 microns/minute.

A particularly advantageous way to provide masking of a pattern for selective etching is to selectively expose the wafer surface to oxygen in the conventional manner, such as by heating in air or oxygen to 1100° C. for 2 hours, to form a silicon dioxide film selectively patterned on the wafer surface prior to depositing the boron nitride. The boron diffusion is thus inhibited by the silica in the selected portion, whereby the masking layer of boron in silicon is formed only on certain areas of the surface.

The etchant EDP etches neat silicon but not the boron doped silicon. Furthermore, etching by such a selective etchant of silicon with a patterned boron diffusion layer results in well defined, smooth cavities and channels. The boron diffusion layers follow <111> planes of <100> oriented silicon wafers. This anisotropy of diffusion makes controlled selective diffusion practical. In a contoured pattern etching with EDP (or other similarly selective etchant) follows the <111> planes with smoothly rounded inside and outside curves bounded by <111> crystal planes on a small scale, compared with the large sharp corners of the prior art. This effect is particularly useful to provide improved microfluidic devices in achieving even, full sweeping flow of gases and liquids.

Figure 5:
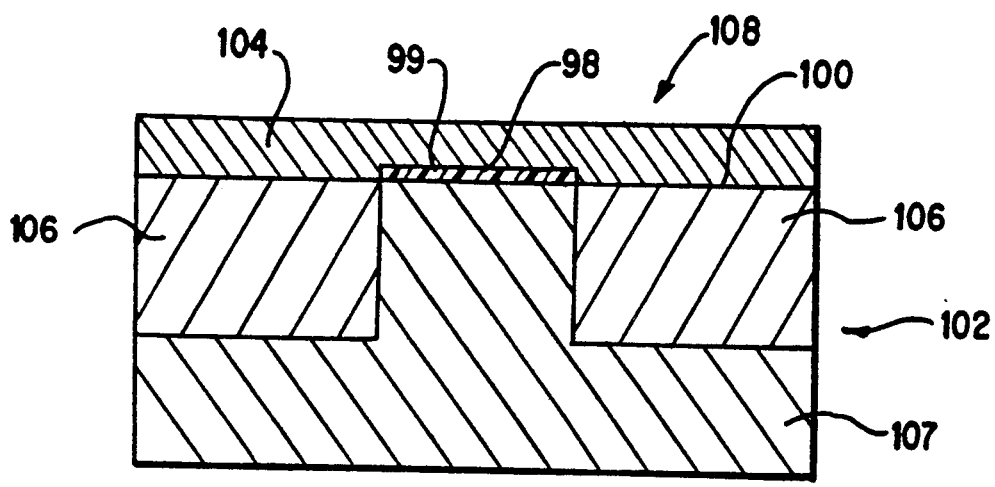
FIG. 5 is a cross section of a laminated structive illustrating steps in a process of the invention.

FIGS. 5 and 6 illustrate the formation of a smooth channel in a device for fluid flow or the like, according to these concepts. With reference to FIG. 5, a silicon dioxide film 98 is deposited in a selected pattern 99 on a clean <100> surface 100 of the wafer member 102. A boron nitride layer 104, is produced at 1100° C. in the manner described herein so that a boron diffusion layer 106 is formed under the boron nitride antithetically to the selected pattern, i.e. where no silicon dioxide is removed, leaving undoped silicon 107 elsewhere. The boron nitride and the silicon dioxide are etched away using a general etchant such as $CF_4/O_2$ and HNA respectively in a selected area 108 (e.g. the entire upper surface in the figure) encompassing at least the pattern 98 and conveniently at least a portion of the boron diffusion layer 106. BN may be left if other processes are planned for further device processing.

The selected area 108 is then exposed to a selective etchant such as EDP to which the boron diffusion layer, is 106 resistant. As shown in FIG. 6 the pattern 99 illustrated has an "S" shape with rounded contours 109. The boron diffusion layer 106, being unetched, forms a step 110 adjacent the etched (i.e. removed) silicon region in the wafer member, with a smooth wall 112 substantially perpendicular to the <100> surface. A thin (2 micron) layer of BN 114 may remain, etched back slightly with a small (1 micron) shoulder 116. A second smooth wall 112' forms the other side of the "S" shaped channel 99 in the wafer. The walls 112 have smooth roundings corresponding to rounded contours of the pattern. With appropriate selection of the contours, such a channel may be used for fluid flow devices, such as the thermal conductivity detector or fluid valve described herein.

Where the boron nitride membrane is not necessary, the boron diffusion layer may be formed by any other available and convenient method on a masked surface of <100> silicon. However use of the hydrogen-free $B_3N$ is quite suitable.

In addition to fluid devices such as for gas chomatography, it will be appreciated that there are many other potential applications for a miniaturized laminated structure according to one or more embodiments of the invention. These include silicon storage devices, ink jet nozzles, fibre-optic couples, laser resonators, thermopile detectors, voltage detectors, pressure transducers, torsion bar and cantilever structures, electron-beam/optical projection assemblies, accelerometers electromechanical switches and thermal print heads.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

What is claimed is:

1. A laminated structure comprising:
   an upper wafer member;
   a lower wafer member, said upper and lower wafer members coupled together so as to define a cavity;
   a membrane, said membrane coupled to said lower wafer member, said membrane being formed of substantially hydrogen-free boron nitride having a nominal composition of $B_3N$, said membrane extending into said cavity between said upper and lower wafer members, said membrane being a structural component inside said cavity.

2. The structure according to claim 1 wherein said laminated structure is a detector for measuring thermal conductivity of a gas, the cavity in said body is adapted to pass a gas therethrough with said boron nitride membrane forming a bridge extending laterally through the cavity, and the device further comprises a thin film resistor being supported by the bridge and receptive of a heating current and voltage measurement to provide a measure of thermal conductivity of the gas.

3. The structure according to claim 1 wherein said laminated structure is a fluid valve, the cavity in the body is adapted to pass a fluid therethrough, the boron nitride membrane extends across the cavity, and the device further comprises distending means for distending the boron nitride membrane into the cavity such to restrict passage of fluid through the cavity.

4. The structure according to claim 3 wherein the cavity is divided into a first cavity and a second cavity by the boron nitride membrane, the second cavity is adapted to pass the fluid therethrough, and the distending means comprises a thermally expandable medium filling the first cavity and further comprises heating means for heating the medium to expand the medium such that the membrane is caused to distend into the second cavity whereby passage of fluid through the second cavity is restricted.

5. The structure according to claim 1 wherein the lower wafer member is formed of single crystal silicon.

6. The structure according to claim 5 further comprising a silicon dioxide film disposed as a bonding layer between the boron nitride membrane and the lower wafer member.

7. The structure according to claim 5 further comprising an intermediate layer disposed between the boron nitride membrane and the lower wafer member, the intermediate layer being formed of boron doped silicon.

8. The structure according to claim 1 wherein the boron nitride membrane is formed by a process comprising depositing by low pressure chemical vapor deposition a hydrogenated boron nitride film on the lower wafer member, and heating the boron nitride film in an environment free of hydrogen and oxygen at a sufficiently high temperature and for a sufficient time period to transform the boron nitride film to the substantially hydrogen-free boron nitride.

9. The structure according to claim 8 wherein the temperature is between about 1050° C. and 1150° C. and the time period exceeds about one hour.

10. A laminated structure comprising:
    an upper wafer member;
    a lower wafer member;
    a middle wafer member, said upper, middle, and lower wafer members coupled together so as to define a cavity;
    a membrane, said membrane coupled to said middle wafer member, said membrane being formed of substantially hydrogen-free boron nitride having a nominal composition of $B_3N$, said membrane extending into said cavity so as to define an upper and a lower portion of said cavity, said upper portion of said cavity located between said upper wafer member and said membrane and adapted to pass a fluid, said lower portion of said cavity extending into said middle wafer member and bounded by said membrane and said lower wafer member;
    a thermally expandable medium filling said lower cavity; and
    means for heating said medium in order to expand said medium so that said membrane distends into said upper cavity and restricts passage of said fluid.

* * * * *